United States Patent
Vock

(10) Patent No.: US 6,188,926 B1
(45) Date of Patent: Feb. 13, 2001

(54) PACEMAKER WITH ADAPTABLE BACKUP PACING IN THE PRESENCE OF ELECTROMAGNETIC INTERFERENCE

(75) Inventor: Josef Vock, Spånga (SE)

(73) Assignee: Pacesetter AB, Järfälla (SE)

( * ) Notice: Under 35 U.S.C. 154(b), the term of this patent shall be extended for 0 days.

(21) Appl. No.: 09/203,353

(22) Filed: Dec. 2, 1998

(30) Foreign Application Priority Data

Dec. 4, 1997 (SE) .................................... 9704520

(51) Int. Cl.$^7$ .................................... A61N 1/362
(52) U.S. Cl. .................................... 607/9
(58) Field of Search .................................... 607/9

(56) References Cited

U.S. PATENT DOCUMENTS

| | | |
|---|---|---|
| 3,661,157 | 5/1972 | Fyson et al. . |
| 4,091,818 | 5/1978 | Brownlee et al. . |
| 4,516,579 | 5/1985 | Irnich . |
| 5,522,857 | 6/1996 | van Krieken . |
| 5,766,227 * | 6/1998 | Nappholz et al. .................. 607/9 |
| 5,836,980 * | 11/1998 | Legay .................. 607/9 |
| 5,978,710 * | 11/1999 | Prutchi et al. .................. 607/17 |

FOREIGN PATENT DOCUMENTS 0 707 866   4/1996   (EP) .
0 713 714   5/1996   (EP) .

OTHER PUBLICATIONS

"User's Manual For Microny SR=", Pacesetter AB (1995).

"Kammertachykardie durch Magnetauflage bei Überprüfung der Schrittmacherfunktion," Kaden, Herzschrittmacher, vol. 6 (1986), pp. 37–38.

"Gefährdung von Herzschrittmacher–Patienten durch Integrierte Kopfhörer–Schwesternrufanlage," Fischer et al, Herzschr. Elektrophys., vol. 2 (1991), pp. 75–76.

"Komplexe Ventrikuläre Herzrhythmusstörungen durch Magnetauflage in der Herzschrittmacher–Überwachung," Bück et al., Herzschr. Elektrophys., vol. 40 (1993), pp. 40–42.

* cited by examiner

Primary Examiner—Carl H. Layno
(74) Attorney, Agent, or Firm—Schiff Hardin & Waite

(57) ABSTRACT

A pacemaker has an interference detecting circuit, and an evaluating and storing unit for continuously evaluating and storing the heart rate. The evaluating and storing unit stores the rate evaluated from at least one of the most recent cardiac cycles free of interference. A determining unit determines an interference backup rate from the stored rate in response to the detection of the onset of an interference situation. A control unit then adjusts the pacing rate equal to the interference backup rate.

6 Claims, 2 Drawing Sheets

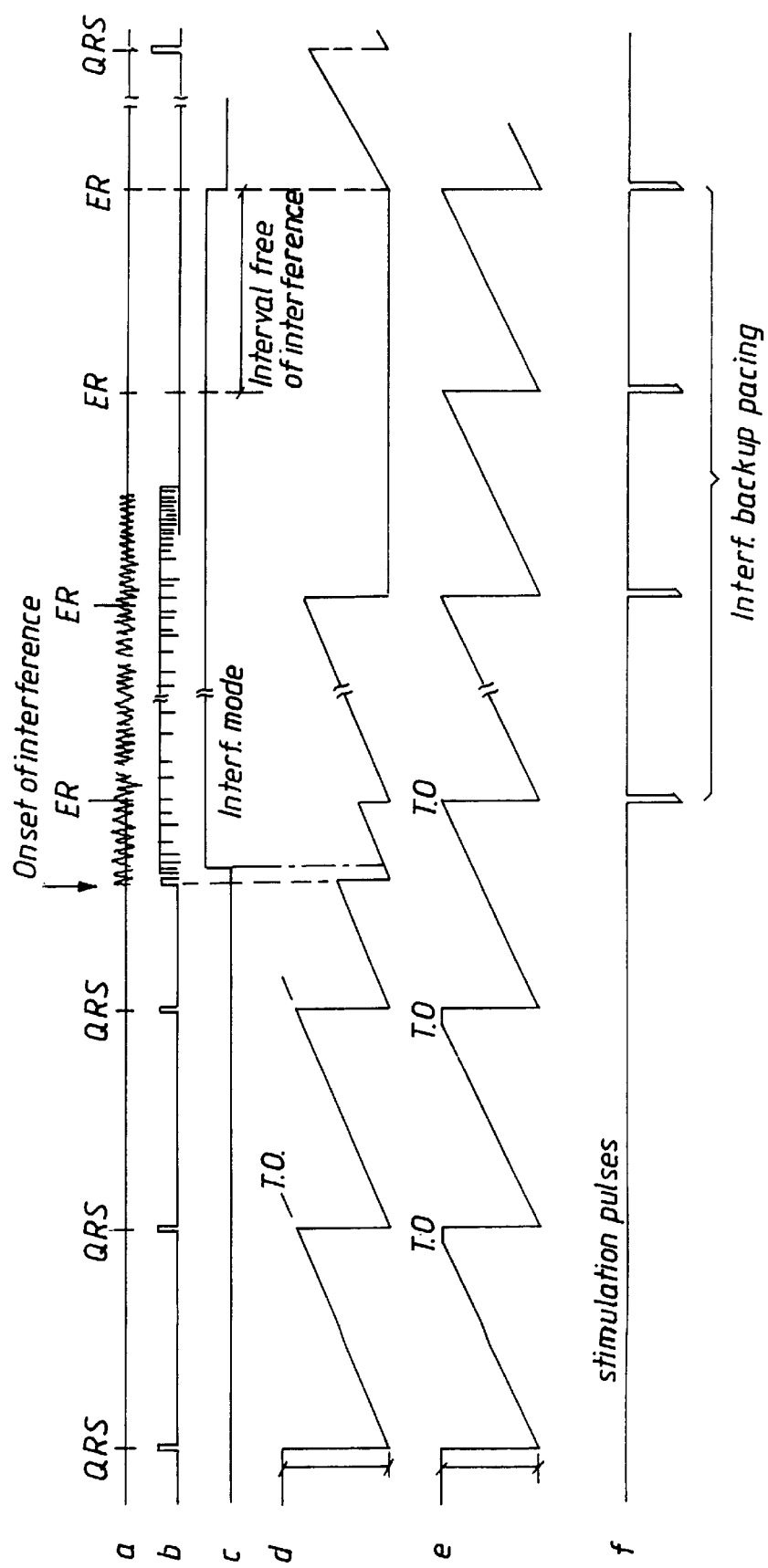

PACEMAKER WITH ADAPTABLE BACKUP PACING IN THE PRESENCE OF ELECTROMAGNETIC INTERFERENCE

BACKGROUND OF THE INVENTION

1. Field of the Invention

The present invention relates to a pacemaker of the type having an interference detecting circuit and an evaluating and storing arrangement for continuously evaluating and storing the heart rate.

2. Description of the Prior Art

It is known to devise pacemakers which, in an interference situation, revert to an "interference backup pacing" mode with a pacing rate equal to the programmed basic rate or equal to a predetermined rate which is somewhat higher than the programmed basic rate. Thus, in U.S. Pat. No. 4,091,818 a cardiac pacing apparatus is described having a first signal processing channel which functions in the demand mode and a second signal processing channel for detecting electromagnetic interference and causing the pacing apparatus to revert to a safe operating rate in the presence of such interference. This operating rate may be an appropriate predetermined fixed rate or a rate-limited rate which is synchronous with the detected electromagnetic interference.

Also U.S. Pat. No. 5,522,857 discloses a pacemaker with circuitry for determining when the sensed signals represent depolarization signals from the patient's heart and when such sensed signals are noise signals and cannot be used for control of the pacemaker. A safety arrangement is provided for controlling the pulse generator to generate a pacing pulse in response to a noise determination that occurs after time out of a predetermined time interval.

From European Application 0 713 714 a control system for medical devices is known in which electromagnetic interference of a biomedical signal used for the control of the device is determined using a correlator. The device is operated in the normal manner as long as the intensity or level of the electromagnetic interference component is such that it does not affect or interfere with the device operation. If the level of the electromagnetic interference exceeds a predetermined threshold the biomedical signal is blanked and a replacement signal, derived from either a previous normal input signal, a stored signal, or a synthesized signal is substituted for the biomedical signal.

U.S. Pat. No. 4,516,579 discloses an interference recognition circuit in a heart pacemaker for improved recognition of certain kinds of interference. The circuit is used for testing sensed heart action signals to recognize the signal as an interfering signal and then rendering the signal ineffective, or recognizing the signal as a true heart action signal and then feeding the signal to a control circuit for the pacemaker.

The backup pacing according to the prior art in interference situations is normally performed at fixed rate and asynchronously to the patient's intrinsic heart activity. Thus the backup pacing is not adapted to the patient's physiological heeds.

Thus, if a patient has e.g. a VVI-pacemaker programmed to a basic rate of 70 bpm and at a given time has an intrinsic heart rate of 85 bpm, the pacemaker will operate in the inhibited mode. If this patient enters into a strong electromagnetic field, as produced e.g. by certain types of anti-theft systems in departmental stores or of any other strong interference source, the pacemaker will not be able to discriminate intrinsic heart activity due to the electromagnetic interference voltages induced in the electrode, but will instead detect the electromagnetic interference during noise sample window and will change the mode of operation to asynchronous VOO-pacing at e.g. 70 bpm. These pacing pulses at the rate of 70 bpm can stimulate within the vulnerable phase of the EGM and induce fibrillation of the patient's heart. A number of cases have been reported in the literature of competitive fixed rate pacing introducing cardiac fibrillation. The same may happen to patients entering a static magnetic field which closes the reed-switch or the equivalent thereof which is inside the pacemaker, with the result that the pacemaker reverts to a fixed magnetic test rate pacing.

Different inductive loop radiators, e.g. electronic article surveillance (EAS) systems, are expected to increase very rapidly in the near future, and even if heart signal detection and discrimination circuits in implanted heart stimulators will become more sophisticated, the number of interference situations nevertheless will increase. This expected development requires a much more sophisticated technique or interference backup pacing in the future, which will decrease the risk of induced fibrillation of the patient's heart.

SUMMARY OF THE INVENTION

It is an object of the present invention to provide a pacemaker which, whenever it experiences such a high level of electromagnetic inference that it becomes unable to sense the intrinsic heart activity, reverts to defined interference operation in a safe way and stimulates with a pacing rate which is well adapted to the patient's intrinsic heart rate or the pacing rate prior to the onset of the interference.

The above object is achieved in accordance with the principles of the present invention in a cardiac pacemaker having pacing circuitry for emitting pacing pulses at an adjustable rate over a number of cardiac cycles, memory for storing the rate for at least one recent cardiac cycle which is free of electromagnetic interference, an electromagnetic interference detector, backup rate determining circuitry for determining, upon detection of electromagnetic interference, a backup rate from the (at least one) rate stored in the memory, and a control unit which is supplied with the backup rate from the back up rate detecting circuitry, which controls the pacing circuitry to set the pacing rate to a rate equal to the backup rate.

Certain rate responsive pacemakers in the art have a feature allowing them, during interference situations, to continue pacing at a sensor controlled rate and therefore should it be noted that the pacemaker according to the invention is particularly useful in non-rate responsive pacemakers.

The pacemaker according to the invention during interference situations provides a pacing rate to the patient which is well adapted to the specific needs of the patient through continuous evaluation, storage and determination of a proper interference backup rate or proper interference backup interval prior to the occurrence of interference. In this way the risk of inducing ventricular fibrillation in the patient due to asynchronous fixed rate interference pacing can be considerably reduced or totally eliminated. The pacemaker according to the invention can be a single as well as a dual chamber pacemaker with unipolar or bipolar electrode configurations.

The improved interference backup pacing of the pacemaker according to the invention can be programmed and tailored to particular needs. For certain pacemaker patients, e.g. those suffering from AV block III, it is not meaningful to evaluate QRS-QRS intervals. In this case it is appropriate, at the onset of an interference situation, to continue to stimulate at a pacing rate which is equal to the latest pacing rate before the onset of the interference.

In an embodiment of a pacemaker according to the invention the evaluating and storing unit stores the rate evaluated from a predetermined number of the most recent cardiac cycles. Thus by calculating the rate during e.g. the last 4–8 pacing cycles without interference and storing this rate, the pacemaker can always be ready for providing asynchronous fixed rate pacing pulses at a suitable rate for the particular patient upon a sudden onset of an interference situation.

In another embodiment of the pacemaker according to the invention, determination unit sets the interference backup rate equal to a rate which is somewhat higher than the average value of the heart rate during the aforementioned number of most recent cardiac cycles. During interference backup pacing the pacing rate is preferably 10% higher than the observed intrinsic pacing rate or the actual pacing rate or rate responsive pacing rate during the latest 4–8 cardiac cycles.

DESCRIPTION OF THE DRAWINGS

FIG. 2 shows different signals as a function of time for explaining the operation of the pacemaker in accordance with the invention.

DESCRIPTION OF THE PREFERRED EMBODIMENTS

Figure 1:
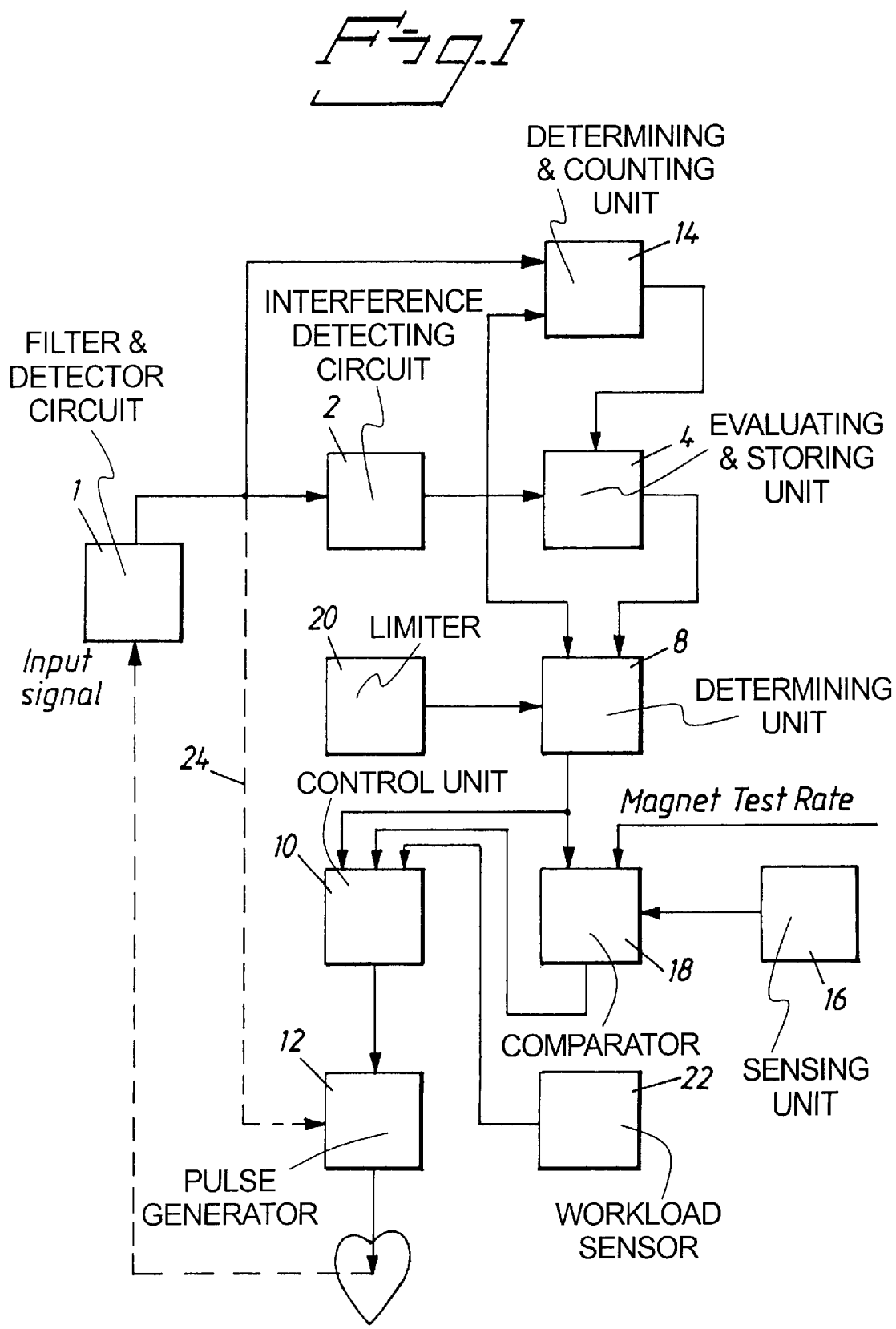
FIG. 1 is a schematic block diagram of a pacemaker constructed and operating in accordance with the principles of the present invention.

The pacemaker according to the invention has an interference detecting circuit 2 to which a cardiac input signal is supplied via an input filter and detector circuit 1. An evaluating and storing unit 4 is connected to the interference detecting circuit 2 for continuously evaluating the heart rate from the input signal and storing this heart rate.

A determining unit 8 is connected to the outputs from the evaluating and storing unit 4 and from the interference detecting circuit 2 for determining an interference backup rate from the stored heart rates in response to the detection of the onset of an interference situation. The calculated interference backup rate is then supplied to a control unit 10 which is connected to the pulse generator 12 of the pacemaker for adjusting the pacing rate equal to the determined interference backup rate when necessary.

As an alternative the determining unit 8 can periodically or continuously determine or calculate an interference backup rate prior to any occurrence of interference and store this determined backup rate value to be used at the detection of the onset of an interference situation.

The input signal is also supplied to a cardiac cycle determining and counting unit 14, which is also connected to the output of the interference detecting circuit 2 for determining and counting cardiac cycles without interference. The determining and counting unit 14 controls the storage of the heart rate in the evaluating and storing unit 4 such that heart rates are determined and stored during a predetermined number of pacing cycles, e.g. 4–8 pacing cycles, without interference, for the interference backup rate determination. In this way the pacemaker is always ready for providing asynchronous, fixed rate pacing pulses at a suitable rate for a particular patient at a sudden onset of an interference situation.

The determining and counting unit 14 preferably controls the evaluating and storing unit 4 such that the evaluated heart rate from the very last cardiac cycle before a detected onset of an interference situation is disregarded. This is a safety measure for insuring that the calculated interference backup rate in a reliable way will be very well adapted to the patient's actual need at the time of the onset of interference.

The determining unit 8 preferably sets the interference backup rate somewhat higher, e.g. 10% higher, compared to the observed intrinsic or pacing rate. Thus in an interference situation the actual pacing rate is somewhat higher than the observed heart rate before the interference situation.

If intrinsic heart activity is present, and the pacemaker is inhibited, the shortest interval, from QRS to QRS or P-pulse to QRS shall be considered when determining the interference backup rate.

Onset of interference is detected in the interference detecting circuit 2 by the use of noise sample windows according to known technique.

If a patient is exposed to a static magnetic field which closes the reed-switch or an equivalent field sensing component, e.g. Hall element, telemetry coil, magnetoresistor, etc., of the pacemaker, a transition to an asynchronous magnetic test rate occurs only if the actual magnet test rate (battery test) is higher than the interference backup rate. A sensing unit 16 is therefore provided to sense closure of the reed-switch and to control a comparator 18 to compare the determined interference backup rate with the predetermined magnet test rate. Transition to magnet test rate then takes place if the test rate exceeds the determined interference backup rate. This feature of the pacemaker according to the invention is preferably programmable such that this function can be disenabled by the physician if it is not desired for a specific patient.

A marker function could also be provided for the case of the magnet test rate being lower than the interference backup rate. In the simplest form the marker can be e.g. one P-pulse (pacing pulse) synchronous with a detected heart signal (QRS) in the case of spontaneous heart activity and in response to application of a magnet. The purpose of this marker function is to make the physician, who wants to perform a magnet test, aware of the fact that the battery test-rate is lower than the calculated interference backup rate. This marker is seen on a surface ECG, but could of course be of another type as well, e.g. one "double" pacing pulse, i.e. two pulses with a short coupling interval of the order of 50–100 msec. The same type of marker, which appears on surface ECG's, can be provided as well for identifying when the stimulation rate prior to the application of the magnet is higher than the battery test rate.

The interference backup rate must be within certain predetermined limits, e.g. always less than 160 bpm, and therefore a limiter 20 is connected to the determining unit 8 for setting the allowed limits for the interference backup rate.

A workload sensor 22 or another physiological rate response sensor controls the stimulation pulse generator 12 to adapt the stimulation rate to the patient's physiological needs.

In the ordinary pacing mode the pacing rate is determined by the heart rate derived from an input signal from this workload sensor 22. This relation is indicated by the dashed line 24.

Additional components of the pacemaker, such as power supply, additional electronics, reed-switch as mentioned above, telemetry circuitry etc. are not shown in the block diagram to simplify FIG. 1, since these components do not directly form any part of the invention.

The operation of a normally inhibited pacemaker designed according to the invention will now be explained with reference to FIG. 2, which shows different signals as a function of time.

Curve a in FIG. 2 thus shows spontaneous heart activity QRS and a period of interference, and curve b the corresponding detected QRS and interference signals. Curve c shows a signal switching between two levels representing normal inhibited operation of the pacemaker according to the invention and an interference mode of operation. Curve d illustrates the time lapse of the number of counts of a counter for determining the programmed basic rate interval of the pacemaker and curve e illustrates the corresponding time lapse for a counter for determining the interference backup interval. Curve f shows stimulation pulses delivered by the pacemaker.

FIG. 2 first illustrates a situation of spontaneous heart activity. Thus QRS complexes are regularly occurring (see curve a), and corresponding signal pulses are detected (see curve b). Each time a QRS complex appears the counter determining the basic rate interval is reset (see curve d). This takes place before the programmed time out (T.O.) of the basic rate interval counter. Thus, the spontaneous heart rate of the patient is higher than the programmed basic rate and the pacemaker operates in inhibited mode as appears from curve f.

Also the interference backup interval counter is reset by the QRS complexes (see curve e). Thus, in this situation the interference backup interval is determined by the QRS-QRS interval.

The interference backup counter is devised to determine an interference backup interval, which is somewhat shorter than the basic rate interval, i.e. the interference backup rate is chosen somewhat higher than the basic heart rate. The interference backup rate can be e.g. 10% higher than the basic rate as mentioned above. In the shown situation the interference backup rate is also somewhat higher than the spontaneous heart activity, and consequently the interference backup interval counter will time out in the period between two consecutive QRS complexes, which appears as a constant level T.O. of a certain extension in curve e immediately before the reset of the interference backup counter.

At a certain time an interference situation starts (see curve a), and an interference mode is detected by the interference detecting circuit, of curve c in FIG. 2. In an interference situation possible spontaneous activity of the heart cannot be reliably detected and the operation of the basic rate interval counter is stopped at a certain level. The timing of the pacemaker is then controlled by the interference backup interval and in this mode of operation stimulation pulses are delivered at each time out T.O. of the interference backup counter as shown by curve f. Corresponding evoked responses ER appear in curve a.

After termination of the interference state the basic rate interval counter will start operation again after a predetermined period provided that no interference is detected in this period, of curves c and d, and the mode of operation free of interference described earlier is resumed.

FIG. 2 illustrates a situation including only spontaneous heart activity and periods of interference. Of course also other situations of cardiac pacing can be managed by the pacemaker according to the invention.

Although modifications and changes may be suggested by those skilled in the art, it is the intention of the inventor to embody within the patent warranted hereon all changes and modifications as reasonably and properly come within the scope of his contribution to the art.

I claim as my invention:

1. A cardiac pacemaker comprising:
   pacing circuitry for emitting pacing pulses at an adjustable rate over a plurality of cardiac cycles;
   a memory for storing said rate for a plurality of most recent cardiac cycles free of electromagnetic interference;
   an electromagnetic interference detector which detects electromagnetic interference;
   backup rate determining circuitry for determining, upon detection of electromagnetic interference by said electromagnetic interference detector, a backup rate from said at least one rate stored in said memory;
   a cardiac cycle determining and counting unit, connected to said memory and to said backup rate detecting circuitry, for supplying a predetermined number of said plurality of most recent cardiac cycles to said backup rate determining circuitry, and wherein said backup rate determining circuitry determines said backup rate from said predetermined number of most recent cardiac cycles; and
   a control unit, supplied with said backup rate from said backup rate determining circuitry, for controlling said pacing circuitry to set said rate equal to said backup rate.

2. A cardiac pacemaker as claimed in claim 1 wherein said plurality of most recent cardiac cycles include a last cardiac cycle immediately preceding a detection of electromagnetic interference by said electromagnetic interference detector, and further comprising means for disregarding said last cardiac cycle before supplying said predetermined number of cardiac cycles to said backup rate detecting circuitry.

3. A cardiac pacemaker as claimed in claim 1 wherein said backup rate determining circuitry comprises means for calculating an average value of said rate over said predetermined number of most recent cardiac cycles, and for setting said interference backup rate higher than said average value.

4. A cardiac pacemaker as claimed in claim 1 further comprising a sensor for sensing a workload of said patient and for controlling said pacing circuitry to adjust said pacing rate in an absence of electromagnetic interference.

5. A cardiac pacemaker as claimed in claim 1 further comprising a limiter connected to said backup rate detecting circuitry for setting an upper limit for said interference backup rate.

6. A cardiac pacemaker comprising:
   pacing circuitry for emitting pacing pulses at an adjustable rate over a plurality of cardiac cycles;
   a memory for storing said rate for at least one recent cardiac cycle free of electromagnetic interference;
   an electromagnetic interference detector which detects electromagnetic interference;
   backup rate determining circuitry for determining, upon detection of electromagnetic interference by said electromagnetic interference detector, a backup rate from said at least one rate stored in said memory;
   a closeable component which closes an electrical circuit in a presence of a magnetic field to initiate a test at a preset test rate;
   sensing means for sensing closure of said closeable component;
   a comparator for comparing said preset test rate to said rate stored in said memory, said comparator producing a comparator result indicating whether said test rate is higher than said rate stored in said memory; and a control unit, supplied with said backup rate from said backup rate determining circuitry, for controlling said pacing circuitry to set said rate equal to said backup rate only if said test rate is higher than said rate stored in said memory.

* * * * *